United States Patent [19]

Engels et al.

[11] Patent Number: 5,039,796

[45] Date of Patent: Aug. 13, 1991

[54] PROCESS FOR 5'-PHOSPHORYLATION OF NUCLEIC ACIDS

[75] Inventors: Joachim Engels, Kronberg/Taunus; Eugen Uhlmann, Glashütten/Taunus, both of Fed. Rep. of Germany

[73] Assignee: Hoechst Aktiengesellschaft, Frankfurt, Fed. Rep. of Germany

[21] Appl. No.: 396,803

[22] Filed: Aug. 21, 1989

Related U.S. Application Data

[63] Continuation of Ser. No. 836,074, Mar. 4, 1986, abandoned.

[30] Foreign Application Priority Data

Mar. 6, 1985 [DE] Fed. Rep. of Germany ....... 3507881

[51] Int. Cl.$^5$ .................. C08H 21/00; C08H 21/02; C08H 21/04
[52] U.S. Cl. ........................ 536/27; 536/28; 536/29
[58] Field of Search .................... 536/27-29

[56] References Cited

U.S. PATENT DOCUMENTS

| | | |
|---|---|---|
| 3,201,435 | 8/1965 | Schulz . |
| 4,321,365 | 3/1982 | Wu et al. ............................. 536/27 |
| 4,415,732 | 11/1983 | Caruthers et al. ................... 536/27 |

FOREIGN PATENT DOCUMENTS

| | | |
|---|---|---|
| 0131993 A2 | 1/1985 | European Pat. Off. . |
| 0196101 | 1/1986 | European Pat. Off. . |
| 1075584 | 9/1960 | Fed. Rep. of Germany . |
| 1252648 | 1/1963 | Fed. Rep. of Germany . |

OTHER PUBLICATIONS

New England Biolabs Catalog, 1985-86, Beverly, Mass., see p. 20.
F. Himmelsbach et al., Tetrahedron Letters, vol. 23, 1982, pp. 4793–4796.
Chemical Abstract 97: 182538q.
Chemical Abstract 95: 168692n.
Chemical Abstract 87: 183904m.
European Search Report in prosecution of corresponding European appln.
Chemical Abstract, vol. 79, No. 53549y.
Chemical Abstract No. 101, No. 230935s.
Chemical Abstract vol. 78, No. 57700t.

*Primary Examiner*—Johnnie R. Brown
*Assistant Examiner*—L. Eric Crane
*Attorney, Agent, or Firm*—Finnegan, Henderson, Farabow, Garrett and Dunner

[57] ABSTRACT

Compounds of the formula

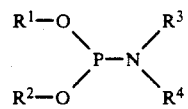

are phosphorylating reagents which react with acylatable hydrogen atoms with elimination of the amine $HNR^3R^4$. The resulting compounds are oxidized to give the corresponding phosphate, thiophosphate or selenophosphate derivatives, and the radicals $R^1$ and $R^2$ are then split off by means of bases. The chemical nature of the radicals $R^1$, $R^2$, $R^3$ and $R^4$ accordingly depends on the requirements for these cleavage reactions.

3 Claims, No Drawings

PROCESS FOR 5′-PHOSPHORYLATION OF NUCLEIC ACIDS

This application is a continuation of application Ser. No. 06/836,074 filed Mar. 4, 1986, now abandoned.

The invention relates to a process for the preparation of esters, thioesters and amides of phosphoric acid, thiophosphoric acid and selenophosphoric acid by reacting acylatable hydroxyl, mercapto and amino compounds with phosphorous acid diester-dialkylamides, oxidizing the resulting phosphorous acid triester, thioester or diesteramide to give the corresponding compound containing pentavalent phosphorus and splitting off by means of bases the two alcoholic or phenolic groups originating from the phosphorylating reagent.

The invention relates in particular to a process for the preparation of compounds of the formula I

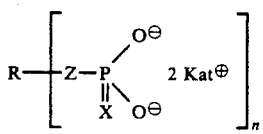

which comprises reacting a compound of the formula II

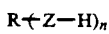

with at least n moles of the phosphorylating reagent of the formula III

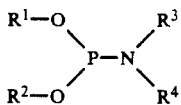

oxidizing the resulting compound of the formula IV

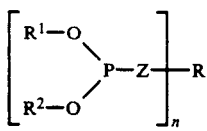

and liberating, by means of bases, the compound of the formula I from the oxidized compounds of the formula V

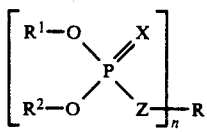

In the formulae mentioned above, the variables have the following meaning:

R is an organic radical carrying no further phosphorylatable hydrogen atoms,

Z represents oxygen, sulfur or —NH—,

Kat represents one molar equivalent of a cation $R^1$ represents a group of the formula IIIa or IIIb

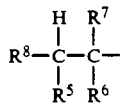

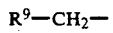

$R^5$, $R^6$ and $R^7$, which can be identical or different, represent hydrogen or methyl, $R^8$ represents a group of the formula IIIc, IIId or IIIe or cyano or Ar

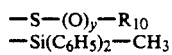

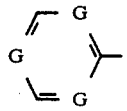

$R^{10}$ denotes lower alkyl or Ar,

G, which can be identical or different, represents C or N, but at least one G represents N, Ar represents phenyl which can be substituted by 1 to 5 identical or different substituents belonging to the series chlorine, fluorine, nitro and cyano, or, in addition to the electron-withdrawings substituents, by one or two lipophilic radicals, n represents 1 or a number greater than 1, y represents 0, 1 or 2, $R^9$ represents a group of the formula IIIf or IIIg $CY_3$      IIIf

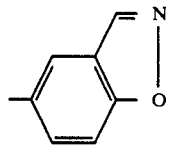    IIIg

Y represents identical or different substituents belonging to the series chlorine, bromine or iodine, $R^2$ can have a meaning of $R^1$ and can then be identical or different, or can denote lower alkyl, a group of the formula IIIh —$CH_2$—Ar      IIIh or Ar, if the latter can be split off more readily by alkalis than $R^1$, $R^5$ and $R^8$ together can represent a group of the formula IIIi

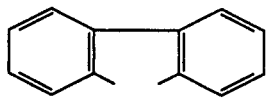

and $R^1$ can also represent methyl if $R^2$ is also methyl.

The nature of the groups $R^3$ and $R^4$ is not critical, provided that the radical —$NR^3R^4$ is split off during the reaction with the compound of the formula II.

$R^3$ and $R^4$, which can be identical or different, represent alkyl having 1 to 8 carbon atoms, cycloalkyl having 5 to 12, preferably up to 8, carbon atoms, benzyl or phenyl or, together with the nitrogen atom to which they are attached, represent a saturated or unsaturated heterocyclic ring which can, if appropriate, contain further heteroatoms and substituents.

Preferred meanings of the variables mentioned above are as follows:

$R^5$, $R^6$ and $R^7$ denote hydrogen, $R^8$ denotes cyano, phenyl or nitrated phenyl, in particular mononitrophenyl, such as p-nitrophenyl, or dinitrophenyl, such as 2,5-dinitrophenyl, chlorinated phenyl, in particular monochlorophenyl, dichlorophenyl or trichlorophenyl, or 2-chloro-4-nitrophenyl and nitrophenyl which is substituted by one or two hydrocarbon radicals, in particular alkane radicals, having 6 to 24, and particularly 12 to 18, carbon atoms.

$R^9$ preferably represents a group of the formula IIIf in which Y preferably represents chlorine.

$R^2$ is lower alkyl, in particular methyl, or it has the meaning of $R^1$ and is then advantageously identical with $R^1$.

$R^3$ and $R^4$ represent alkyl having 1 to 6 carbon atoms, especially lower alkyl, cyclohexyl, benzyl or phenyl, and, together with the nitrogen atom, represent pyrrolidyl, piperidyl, morpholyl, triazolo, benzotriazolo or tetrazolo, it being possible for the aromatic radicals to be substituted by chlorine, fluorine, nitro or cyano.

The expression "lower" represents radicals having up to 4 carbon atoms.

X and Z preferably represent oxygen.

n represents 1 to 6, especially 1 or 2 and particularly 1.

The compounds of the formula III in which $R^1$ is other than methyl are new, as are also the compounds of the formula VI. The invention also relates to these new compounds.

Compounds of the formula V in which $R^1$ and $R^2$ represent 2-(4-nitrophenyl)-ethyl, X and Z represent oxygen and R represents a thymidyl radical are disclosed by F. Himmelsbach et al., Tetrahedron Letters 23 (1982) 4793–4796. These compounds are obtained by reacting thymidine with bis-(p-nitrophenylethyl) phosphoromonochloridate, wherein the hydroxyl group in the 5'-position is primarily acylated. This phosphorylating reagent is rather labile and could neither be distilled under high vacuum nor be prepared in a solid form. If phosphorus trichloride is used as the starting material, the preparation of compounds of the formula V requires five reaction stages by the known route, whereas these compounds can be prepared in four stages by the route according to the invention.

In accordance with the literature reference mentioned, the compounds of the formula V are then reacted further to give oligonucleotides and, finally, the p-nitrophenylethyl groups are split off from the latter by means of 1,5-diazabioyolo-[5,4,0]undec-5-ene (DBU).

The compounds of the formula III are accessible by methods known per se from phosphorus trichloride by reacting the latter with the hydroxyl compounds $R^1$—OH and $R^2$—OH and the secondary amine H—$NR^3R^4$. Instead of the free secondary amine it is also possible to employ a corresponding silyl compound. The sequence of replacement of the chlorine atoms in the phosphorus trichloride depends on the reactivity of the hydroxyl or amino compounds. Thus, for example, the compound of the formula VI

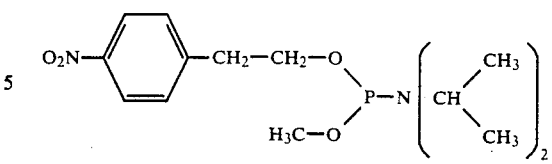

can be obtained by the following routes:

a) phosphorus trichloride is first reacted with methanol in the presence of a base, and the reaction product is reacted with diisopropylamine and then with 2-(p-nitrophenyl)-ethanol in the presence of a base, b) phosphorus trichloride is first reacted with 2-(p-nitrophenyl)-ethanol, then with diisopropylamine and finally with methanol, or c) phosphorus trichloride is first reacted with diisopropylamine and the product is then reacted with 2-(p-nitrophenyl)-ethanol and then with methanol.

The reaction of the phosphorylating reagent of the general formula III with a hydroxyl compound is effected either in solution using an equimolar amount or a slight excess of, for example, up to 50, preferably up to 25, mol % of phosphorylating reagent in the presence of a weak acid such as tetrazole, or an amine hydrochloride or, in the form of a solid phase synthesis, using a large excess of phosphorylating reagent in the presence of a weak acid. If, for example, the hydroxyl component is attached to a carrier, the phosphorylating reagent is employed in a 10-fold to 20-fold molar excess. If the reaction is carried out in solution, the solvent must, of course, be inert towards the phosphorylating reagent and the component to be acylated. The reaction is carried out at temperatures from −80 to +80° C., preferably −20 to +50° C. and particularly 0 to 25° C.

Depending on the choice of the radicals $R^1$ and $R^2$, the phosphorylation product of the formula IV has a more or less pronounced lipophilic character, particularly if $R^8$ represents phenyl which has lipophilic substituents. These lipophilic compounds can be separated readily from the non-phosphorylated starting materials, for example by chromatography, such as high pressure liquid chromatography on "reversed phase" material, for example commercial silica gel containing octadecylsilyl groups.

The choice of the substituents $R^1$ and $R^2$ depends, of course, on the chemical nature of the radical R, i.e. on the compound into which the phosphate group is to be introduced. The definiton of R as a group which does not contain further phosphorylatable H-Z groups is to be understood as meaning that the phosphorylating reagent of the formula III acylates in a relatively non-specific manner and, therefore, in a selective phosphorylation reaction, the hydrogen atoms have been replaced by appropriate protective groups in any further phosphorylatable Z-H groups which may be present. Z-H groups which are "phosphorylatable" are to be understood here as meaning Z-H groups which are capable of reacting under the conditions of acylation—Z-H groups whose reactivity has been impaired by steric hindrance or by inactivating groups are therefore intended to be excluded.

Since the radicals $R^1$ and $R^2$ are in most cases split off by means of a base in order to liberate the phosphate group, the nature of the radicals $R^1$ and $R^2$ and of the base employed depends on the sensitivity of the radical R. If R is adequately stable, the scission can, accordingly, be carried out by means of aqueous alkali solutions, and thereby the choice of $R^1$ and $R^2$ is also relatively non-critical. If there are sensitive groups on the radical R, the reaction will be carried out in a manner known per se under correspondingly mild conditions, for example in a non-aqueous system and using a suitable base, for example DBU, which is disclosed in the literature reference mentioned above.

The scission of the radicals $R^1$ and $R^2$ is effected by methods which are known per se:

The scission of a methyl radical from a phosphate triester can be effected by means of thiophenol or thiocresol in the presence of a base, such as triethylamine. This reaction is expediently carried out at temperatures from $-100$ to $+100°$ C., preferably at $-60$ to $+60°$ C. and especially at $-20$ to $+30°$ C. The groups which can be removed in a β-elimination reaction, i.e., for example, compounds in which the group IIIb is present, are removed by means of metals such as zinc or by voltage-controlled electrolytic reduction. This reaction is advantageously carried out at temperatures from $-50$ to $+80°$ C., preferably at $-20$ to $+50°$ C. and especially at 0 to 30° C. Ethyl groups containing electronegative substituents can be removed by means of nonnucleophilic bases, which can also be attached to polymeric carriers. This reaction is advantageously effected at temperatures from $-60$ to $+100°$ C., preferably at $-20$ to 50° C. and especially at 0 to 30° C.

When ethyl groups containing electronegative substituents are split off from compounds of the formula V it is advantageous to employ the following bases, which are listed in order of decreasing reactivity:

a) cyclic phosphoric acid triamide-imides of the formula VII

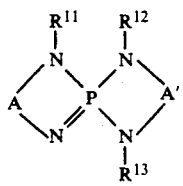

in which $R^{11}$, $R^{12}$ and $R^{13}$ denote identical or different lower alkyl groups, preferably methyl or ethyl, and A and A' denote lower alkylene groups having 2 to 4 carbon atoms in the chain, preferably 1,3-propylene, b) 1,5,7-triazabicyclo[4,4,0]dec-5-ene (TBD) and also 7-methyl-1,5,7-triazabicyclo[4,4,0]dec-5-ene, c) 1,5-diazabicyclo[4,3,0]non-5-ene (DBN), DBU and also lower alkali metal alcoholates, in particular sodium alkanolates and potassium alkanolates, such as sodium methylate, sodium ethylate or potassium tertiary butylate, and d) 1,1,3,3-tetramethylguanidine.

Compounds in which $R^1$ and, if appropriate, also $R^2$ are β-cyanoethyl can be split by means of ammonia and are therefore preferably employed in cases where other protective groups are split off by means of ammonia.

A great advantage of the process according to the invention lies in the fact that sensitive compounds can be phosphorylated. As has been indicated above in the scission of the radicals $R^1$ and $R^2$ by means of bases, the process according to the invention permits a multiplicity of embodiments, so that the individual reaction stages can be coordinated with further reactions at the radical R. This aspect is relevant not only for the scission of the radicals $R^1$ and $R^2$, but equally for the oxidation reaction and—if desired—for the introduction of more than one phosphate group.

A further considerable advantage of the invention can be seen in the fact that it is possible to introduce, not only the phosphate group itself, but also the thiophosphate and selenophosphate groups. This affords a simple route to chemical analogs of natural substances which are not accessible, for example, by the process of Himmelsbach et al.

The oxidation of the compounds of the general formula IV to give the phosphates of the general formula V (X=0) is effected in the manner known for analogous compounds. Examples of oxidizing agents which can be used are dinitrogen tetroxide or iodine, but especially peroxides, above all anhydrous t-butyl hydroperoxide. The reaction is preferably carried out in a moderately polar solvent, for example nitriles, such as acetonitrile, or halogenated, especially chlorinated, lower hydrocarbons, such as chloroform. This reaction is advantageously carried out at temperatures from $-100$ to $+100°$ C., preferably at $-50$ to $+60°$ C. and especially at $-20$ to $+30°$ C.

The preparation of compounds of the general formula V in which X denotes sulfur or selenium is effected by direct reaction between the compounds of the general formula IV and elementary sulfur or selenium. Stirring in a polar solvent, such as tetrahydrofuran, with the stoichiometric amount of sulfur or selenium results in good yields of the corresponding thiophosphates or selenophosphates of the general formula V. This reaction is advantageously carried out at temperatures from $-100$ to $+100°$ C., preferably at $-50$ to $+60°$ C. and especially at $-20$ to $+30°$ C.

It has already been emphasized that the invention enables the chemical nature of the radical R to be taken into consideration to a considerable extent, and that this radical can also carry sensitive groups or molecular moieties. Suitable starting materials of the formula II are, accordingly, aliphatic or aromatic hydroxyl, mercapto and amino compounds, i.e. alcohols, phenols, mercaptans, thiophenols and aliphatic and aromatic amines. Natural substances or compounds analogous to natural substances, for example steroid derivatives, phospholipids and, above all, sugars and sugar derivatives, such as nucleosides, nucleotides, oligonucleotides or polynucleotides, can be phosphorylated particularly advantageously.

The preparation of nucleotides containing a terminal, unprotected phosphate group by means of the currently used combination of phosphate protective groups, in accordance with the phosphite process, is only possible with an enormous additional effort, or not at all. Nor does the o-chlorophenyl β-cyanoethyl phosphate combination of protective groups, which is frequently used in triester synthesis, afford terminal phosphates, since the hydrolysis of the o-chlorophenyl group while maintaining the β-cyanoethyl group is not possible.

The phosphorylation of the terminal 5'-hydroxyl group has therefore been carried out in accordance with the methods known hitherto by means of a nucleoside triphosphate, usually adenosine triphosphate, and a kinase, such as (T4)-polynucleotide kinase. This process is rather expensive.

In accordance with the invention, the phosphorylation of the 5'-hydroxyl group can now be carried out by chemical means, not only on the isolated oligonucleotide, but even on the compound still attached to the carrier. The process according to the invention takes place under conditions so mild that the nucleoside, nucleotide, oligonucleotide or polynucleotide is not damaged.

However, the invention also permits the introduction of phosphate groups into nucleosides or monomeric, oligomeric or polymeric nucleotides at another point, for example by phosphorylating the 3'-hydroxyl group or groups or, in the case of ribonucleosides or ribonucleotides, permits introduction into the 2'-position.

In the Examples which follow, the invention is illustrated in greater detail in the field, known to be difficult, of the nucleotides. This is in no way to be regarded as a limitation, however, since the phosphorylation of nucleotides is representative in a very general way of the introduction of phosphate groups.

Preparation of the phosphorylating reagents of the general formula III

EXAMPLE 1

Phosphorous acid methyl ester-diisopropylamide-chloride 127 g (0.96 mol) of phosphorous acid methyl ester-dichloride are initially taken in a mixture of 250 ml of absolute ether and 250 ml of absolute pentane, and a solution of 270 ml (1.92 mol) of diisopropylamine in 100 ml of absolute ether and 100 ml of absolute pentane is added dropwise in the course of 2 hours at $-15°$ C., with vigorous stirring and nitrogen blanketing. The reaction mixture is allowed to heat up to room temperature while being stirred, and is then stirred for a further 2 hours. It is then cooled to $-15°$ C. again, and the hydrochloride is removed from the reaction solution by filtration under an inert gas. The filter cake is rinsed with 750 ml of a cold mixture of equal volumes of absolute ether and absolute pentane. The filtrates are combined, and the solvents are removed under a water pump vacuum. The residue is subjected twice to a high-vacuum distillation through an 80 cm Vigreux column. This gives 80 g of a main fraction (boiling point 38 to 41° C. at 0.1 mbar) which, according to $^{31}$P-NMR, is composed of 99% of a single substance ($\delta=185$ ppm).

EXAMPLE 2

Phosphorous acid methyl ester-[(p-nitrophenyl)-ethyl ester]-diisopropylamide (formula VI)

5.01 g (30 mmol) of thoroughly dried 2-(p-nitrophenyl)ethanol are dissolved in 60 ml of freshly distilled methylene chloride, and 24 ml of diisopropylethylamine are added. The mixture is cooled to about 0° C. and 6 ml (33 mmol) of phosphorous acid methyl ester-diisopropylamide-chloride are added dropwise in the course of 5 minutes, with stirring, and the mixture is stirred for a further 10 minutes at this temperature. The reaction mixture is then diluted with 750 ml of ethyl acetate, previously washed with 450 ml of pH 7 phosphate buffer. The ethyl acetate phase is extracted three times by shaking with 450 ml of phosphate buffer (pH 7), and is dried over sodium sulfate and concentrated. The resulting oil is dried in a high vacuum at 30° C. This gives 9 g of oil which, according to $^{31}$P-NMR, is 86% pure. The product can be concentrated further ($^{31}$P-NMR: 95% pure) by chromatography over a short silica gel column which has been equilibrated with ethyl acetate/methylene chloride/triethylamine in a ratio by volume of 5:4:1, using the same system as the mobile phase. This gives an oil which solidifies in a refrigerator ($-20°$ C.).

$^{31}$P-NMR: $\delta = 149$ ppm
$^{1}$H-NMR:
P—O—CH$_2$—CH$_2$— $\delta = 3.75$ ppm, m [2]
P—O—CH$_2$—CH$_2$— $\delta = 2.98$ ppm, t [2]
P—OCH$_3$ $\delta = 3.35$ ppm, d [3]

m = multiplet [intensity]
s = singlet
d = doublet
t = triplet

EXAMPLE 3

Phosphorous acid methyl ester-2-cyanoethyl-ester-diisopropylamide (formula VIII)

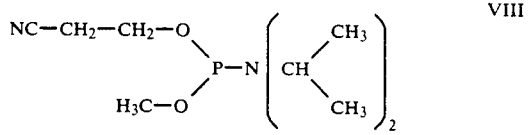

0.68 ml (10 mmol) of 2-cyanoethanol are reacted analogously to Example 2 with 2 ml (11 mmol) of phosphorous acid methyl ester-diisopropylamide-chloride in the presence of 8 ml of diisopropylethylamine in 20 ml of freshly distilled methylene chloride. Drying at 30° C. in a high vacuum gives 2.5 g of an oil which, according to $^{31}$P-NMR, contains 94% of the compound VIII.

$^{31}$P-NMR: $\delta = 150$ ppm
$^{1H}$-NMR:
P—OCH$_2$CH$_2$—CN $\delta = 3.75$ ppm, m [2]
P—OCH$_2$CH$_2$—CN $\delta = 2.60$ ppm, t [2]
P—OCH$_3$ $\delta = 3.35$ ppm, d [3]

EXAMPLE 4

Phosphorous acid 2-(p-nitrophenyl)-ethylester-dichloride 5 g (30 mmol) of 2-(p-nitrophenyl)-ethanol are dissolved in 100 ml of absolute ether and are reacted, in the course of 40 minutes, at $-20$ to $-30°$ C. and with stirring, with 25.5 ml (150 mmol) of freshly distilled phosphorus trichloride, added dropwise. The ether is removed at 0° C. under a water pump vacuum and the excess phosphorus trichloride is then removed under a high vacuum and the residual oil is dried in a high vacuum.

$^{31}$P-NMR $\delta = 179.8$ ppm 93% of the total P.

EXAMPLE 5

Phosphorous acid diisopropylamide-dichloride 87 ml (1 mol) of phosphorus trichloride are dissolved in 800 ml of petroleum ether, the solution is cooled to 5° C. and a solution of 283 ml (2 mol) of diisopropylamine in 660 ml of petroleum ether is then added dropwise while stirring in the course of one hour at 5° C. Stirring is continued for one hour at this temperature, the precipitated amine hydrochloride is filtered off, the petroleum ether is removed under a water pump vacuum and the residue is distilled in vacuo (0.2 mbar). The main fraction obtained, at 38 to 41° C., is 98 g of an oil which crystallizes on standing in a refrigerator (−20° C.) and is 99% pure ($^{31}$P-NMR, δ=170 ppm).

EXAMPLE 6

Phosphorous acid bis-[2-(p-nitrophenyl)-ethyl ester]-diisopropylamide (formula IX)

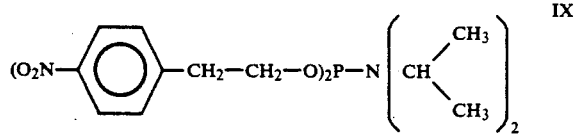

26 ml (0.15 mol) of diisopropylethylamine are added to a solution of 16 g (0.1 mol) of 2-(p-nitrophenyl)-ethanol in 40 ml of absolute tetrahydrofuran, and the mixture is cooled to 0° C. 10 g (0.05 mol) of phosphorous acid diisopropylamide-dichloride are added in the course of 15 minutes, with stirring. The reaction mixture is then allowed to come to room temperature and to react further for about 30 minutes. The amine hydrochloride is filtered off with suction, the filter cake is washed with a little tetrahydrofuran, and the combined filtrates are concentrated to give a solid residue. 1 g of this residue is purified by column chromatography over 70 g of silica gel using toluene/n-hexane/triethylamine in a ratio by volume of 7:2:1. This gives 0.95 g of a powder which, according to $^{31}$P-NMR, is 96% pure.

$^{31}$P-NMR: δ = 147.5 ppm
$^{1}$H-NMR: P—OCH$_2$CH$_2$—    δ = 3.85 ppm, m [4]
         P—OCH$_2$CH$_2$—    δ = 2.98 ppm, t [4]
         P—N—CH           δ = 3.5 ppm, m [2]
         P—N—CH(CH$_3$)$_2$.  δ = 1.13 ppm, d [12]

Phosphorylation reactions

Chemical synthesis of a single-stranded oligonucleotide containing a 5'-phosphate radical: NcoI-linker 5' pCCATGG 3'

EXAMPLE 7

The nucleoside located at the 3'-end, in the present case thus guanosine, is attached to "controlled pore glass" (CPG, made by Pierce) by a covalent link via the 3'-hydroxyl group by the method of M.J. Gait et al.; Nucleic Acids Res. 8 (1980); 1081–1096.

This is effected by first reacting the silica gel with 3-(triethoxysilyl)-propylamine with the elimination of ethanol, an Si—O—Si bond being formed. The guanosine is reacted in the form of the N$^{2'}$-isobutyryl-3'-O-succinoyl-5'-dimethoxytrityl ether with the modified carrier in the presence of paranitrophenol and N,N'-dicyclohexylcarbodiimide, the free carboxyl group of the succinoyl group acylating the amino radical of the propylamine group.

In the following stages of the synthesis, the base component is employed in the form of 5'-O-dimethoxytrityl-nucleoside-3'-phosphorous acid monomethyl ester-dialkylamide or ester-dichloride, the adenine being present as the N$^6$-benzoyl compound, the cytosine as the N$^4$-benzoyl compound, the guanine as the N$^2$-isobutyryl compound and the thymine, which does not contain an amino group, being present without a protective group.

The reaction cycle for the construction of the oligonucleotide chain is as follows: 25 mg of the polymeric carrier, containing 1 μmol of guanosine attached, are treated successively with the following agents:

a) nitromethane
b) 3% solution of trichloroacetic acid in 1,2-dichloroethane
c) nitromethane
d) acetonitrile
e) 10 to 20 μmol of the corresponding nucleoside phosphite and 100 μmol of tetrazole in 0.2 ml of anhydrous acetonitrile (5 minutes)
f) 20% solution of acetic anhydride in tetrahydrofuran containing 40% of lutidine and 10% of dimethylaminopyridine (2 minutes)
g) acetonitrile
h) tetrahydrofuran containing 20% of water and 40% of lutidine
i) 3% solution of iodine in collidine/water/tetrahydrofuran in a ratio by volume of 5:4:1 (0.5 minute)
j) acetonitrile "Phosphite" is understood in this connection to be deoxyribose-3'-monophosphorous acid monomethyl ester, the third valency being saturated by chlorine or a tertiary amino group, for example a morpholino radical. The yields in each of the various stages of the synthesis can be determined by spectrophotometry after the detritylation reaction (b) by measuring the absorption of the dimethoxytrityl cation at a wavelength of 496 nm.

The reaction cycle for the chemical phosphorylation of the 5'-hydroxyl group is effected in principle as in the preceding Examples, but with the difference that, firstly, 20 μmol of the corresponding phosphorylating reagent (for example the compound VI) and 100 μmol of tetrazole are reacted in 0.2 ml of anhydrous tetrahydrofuran/acetonitrile (mixture of equal volumes) for 10 to 20 minutes in e) and, secondly, stage f) is omitted and, thirdly, the time in stage i) is prolonged to 5 minutes.

When the synthesis of the oligonucleotide has been completed, the methyl phosphate protective groups of the oligomer are split off by means of p-thiocresol and triethylamine. The oligonucleotide is then separated from the solid carrier by treatment with ammonia for 3 hours. The amino protective groups of the bases are split off quantitatively by treating the oligomer with concentrated ammonia for 2 to 3 days.

a) In the case of the phosphorylating reagent phosphorous acid methyl ester-[2-(p-nitrophenyl)-ethyl ester]-diisopropylamide (VI), an oligonucleotide having a 2-(p-nitrophenyl)-ethyl phosphate radical on the 5'-hydroxyl group is obtained after this elimination of protective groups. This phosphate ester can be purified by HPLC on "reversed phase" material, which results in a particularly good removal of the hydroxyl component. The p-nitrophenylethyl group is split off by treating the ester with 0.9 M TBD in pyridine/water in a ratio by volume of 9:1 for 8 hours at room temperature. After this, starting material is no longer present according to HPLC or gel electrophoresis on a 20% strength polyacrylamide gel with 7 M urea. 1 ml of 2 M acetic acid is added to the reaction mixture, and the latter is concentrated. The residue is freed from salts over a column containing $^R$SEPHADEX G 50 using 0.02 M triethylammonium bicarbonate (pH 7) as the mobile phase.

The resulting 5'-phosphate-oligonucleotide can be polymerized by means of polynucleotide ligase to give double-stranded, repetitive DNA, which can then be cut again with the restriction enzyme Hae III (cutting site: GG ↓ CC).

b) In the case of the phosphorylating reagent phosphorous acid methyl ester-2-cyanoethyl-ester-diisopropylamide (VIII) and of phosphorous acid bis-(2-cyanoethyl ester)diisopropylamide (X)

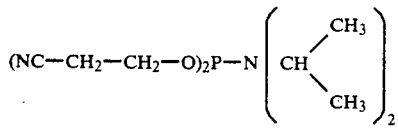

the free 5'-phosphate p CCATGG is obtained immediately after the ammonia cleavage (concentrated ammonia for 3 days at room temperature or for 10 hours at 75° C.).

c) In the case of the reagent phosphorous acid bis-[2-(p-nitrophenyl)-ethyl ester]-diisopropylamide (IX), the phosphate 2-(p-nitrophenyl)-ethyl ester is also obtained after the thiophenolate and ammonia treatment, and this ester can in turn be split by means of a suitable base, such as DBU or TBD, to give the 5'-phosphate, free from protective groups.

We claim:

1. A process for the preparation of compounds of the formula I

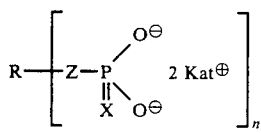

in which

Kat represents one molar equivalent of a cation,

R is an organic radical which carries no further phosphorylatable hydrogen atoms, X represents oxygen, sulfur or selenium, X represents oxygen, sulfur or —NH— and n is 1 to 6, which comprises reacting in the presence of weak acid, a compound of the formula II R—(Z—H)$_n$      II with at least n moles of the phosphorylating reagent of the formula III

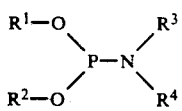

in which

R$^1$ represents a group of the formula IIIa or IIIb

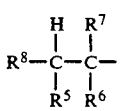

R$^9$—CH$_2$—      IIIb

R$^5$, R$^6$ and R$^7$, which can be identical or different, denote hydrogen or methyl, R$^8$ denotes of the formula IIIc, IIId, or IIIe or cyano or Ar, —S—(O)$_y$—R$_{10}$      IIIc
—Si(C$_6$H$_5$)$_2$—CH$_3$      IIId

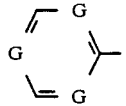

R$^{10}$ denotes lower alkyl or Ar,

G, which can be identical or different, denotes C or N, but at least one G represents N, Ar denotes phenyl which can be substituted by 1 to 5 identical or different substituents belonging to the series chlorine, fluorine, nitro and cyano or, in addition to the election-withdrawing substituents, can be substituted by branched or unbranched alkyl with 8 to 24 carbon atoms y is 0, 1 or 2, R$^9$ denotes a group of the formula IIIf or IIIg CY$_3$      IIIf

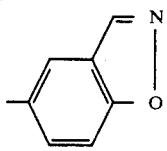

Y denotes identical or different substituents belonging to the series chlorine, bromine or iodine, R$^2$ can have a meaning of R$^1$ and is then identical or different, or denotes lower alkyl, a group of the formula IIIh —CH$_2$—Ar      IIIh or Ar, if the latter can be removed by alkaline hydrolysis at a higher rate, under alkaline conditions, than R$^1$ by alkalis, R$^5$ and R$^8$ together represent a group of the formula IIIi

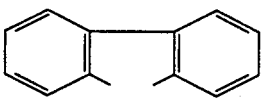

and R$^1$ also represents methyl if R$^2$ is also methyl, and R$^3$ and R$^4$, which can be identical or different, denote alkyl having 1 to 8 carbon atoms, cycloalkyl having 5 to 12 carbon atoms, benzyl or phenyl or, together with the nitrogen atom to which they are attached, denote a saturated or unsaturated heterocyclic ring which can contain further heteroatoms and substituents, oxidizing the resulting compound of the formula IV

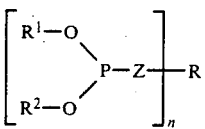

in which $R^1$, $R^2$, R, Z and n have the meanings mentioned and liberating the compound of the formula I by means of bases from the oxidized compounds of the formula V

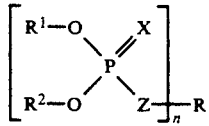

in which n, $R^1$, $R^2$, X, Z and R have the meanings mentioned.

2. The process of claim 1, in which in formula IV
$R^5$, $R^6$ and $R^7$ are hydrogen,
$R^8$ is cyano, phenyl or phenyl which is substituted by nitro, chlorine or one or two hydrocarbon radicals having 8 to 24 carbon atoms,
$R^9$ is a group of the formula IIIf,
$R^2$ is a lower alkyl or has the meaning of $R^1$, and
n is 1 or 2.

3. The process of claim 2, wherein
$R^8$ is mononitrophenyl, dinitrophenyl, monochlorophenyl, dichlorophenyl, trichlorophenyl or 2-chloro-4-nitrophenyl or phenyl which, in addition to electron-withdrawing substituents, is substituted by one or two hydrocarbon radicals having 12 to 18 carbon atoms,
$R^9$ is trichloromethyl,
$R^2$ is methyl, and
$R^3$ and $R^4$ are lower alkyl.

* * * * *

UNITED STATES PATENT AND TRADEMARK OFFICE
CERTIFICATE OF CORRECTION

PATENT NO.  : 5,039,796
DATED       : August 13, 1991
INVENTOR(S) : Joachim Engels et al.

It is certified that error appears in the above-identified patent and that said Letters Patent is hereby corrected as shown below:

Title page: Assignee, change "Frankfurt" to --Frankfurt am Main--.

Claim 1, column 11, line 42, change "X" to --Z--.

Claim 1, column 11, line 44, before "weak" insert --a--.

Claim 1, column 12, line 1, after "denotes" insert --a group--.

Claim 1, column 12, line 40, change "$-CH_z-Ar$" to -- $-CH_2-Ar$ --.

UNITED STATES PATENT AND TRADEMARK OFFICE
CERTIFICATE OF CORRECTION

PATENT NO. : 5,039,796

DATED : August 13, 1991

INVENTOR(S) : Joachim Engels, et al.

It is certified that error appears in the above-identified patent and that said Letters Patent is hereby corrected as shown below:

Column 14, claim 2, line 5, before "lower" delete "a".

Signed and Sealed this

Sixth Day of July, 1993

*Attest:*

MICHAEL K. KIRK

*Attesting Officer*     *Acting Commissioner of Patents and Trademarks*